(12) United States Patent
Berti

(10) Patent No.: US 7,260,178 B2
(45) Date of Patent: Aug. 21, 2007

(54) DIFFRACTOMETER AND METHOD FOR DIFFRACTION ANALYSIS

(75) Inventor: Giovanni Berti, Pisa (IT)

(73) Assignee: XRD-Tools S.R.L., Casina (IT)

( * ) Notice: Subject to any disclaimer, the term of this patent is extended or adjusted under 35 U.S.C. 154(b) by 0 days.

(21) Appl. No.: 10/502,101

(22) PCT Filed: Jan. 21, 2003

(86) PCT No.: PCT/EP03/00546

§ 371 (c)(1),
(2), (4) Date: Feb. 15, 2005

(87) PCT Pub. No.: WO03/060498

PCT Pub. Date: Jul. 24, 2003

(65) Prior Publication Data

US 2005/0141667 A1   Jun. 30, 2005

(30) Foreign Application Priority Data

Jan. 21, 2002   (IT) .......................... MI2002A0097

(51) Int. Cl.
*G01N 23/20* (2006.01)
*G01T 5/00* (2006.01)

(52) U.S. Cl. ............................ 378/71; 378/72; 378/73; 250/305; 250/306; 250/390.09

(58) Field of Classification Search ................... 378/79, 378/80, 81, 71, 72, 73; 250/305, 306, 390.09
See application file for complete search history.

(56) References Cited

U.S. PATENT DOCUMENTS

| 2,843,749 A | * | 7/1958 | Koblenz ...................... 378/49 |
| 4,769,832 A | | 9/1988 | Louiday |
| 4,922,512 A | | 5/1990 | Lajus et al. |
| 5,014,293 A | | 5/1991 | Boyd et al. |
| 5,359,640 A | * | 10/1994 | Fink et al. ..................... 378/79 |
| 6,064,717 A | | 5/2000 | Ortega et al. |
| 6,072,854 A | * | 6/2000 | Kikuchi et al. ............... 378/79 |

FOREIGN PATENT DOCUMENTS

| EP | 1016375 A1 | 5/2000 |
| GB | 2198920 A | 6/1988 |

* cited by examiner

Primary Examiner—Chih-Cheng G Kao
(74) Attorney, Agent, or Firm—Duane C. Basch; Basch & Nickerson LLP

(57) ABSTRACT

Diffractometer and method for diffraction analysis making use of two Euler cradles, a primary and a secondary Euler cradle. The primary Euler cradle supports a source of a radiation beam, having a collimation axis, and a radiation beam detector, having a reception axis, said collimation and reception axis, conveying in a centre of the diffractometer which is fixed with respect to the primary Euler cradle. The source and detector are adapted to move along the primary Euler cradle. The secondary Euler cradle supports the primary Euler cradle and is arranged to rotate the latter.

15 Claims, 4 Drawing Sheets

DIFFRACTOMETER AND METHOD FOR DIFFRACTION ANALYSIS

FIELD OF THE INVENTION

The present invention concerns a diffractometer, in particular an x-ray diffractometer. In more detail, it concerns a diffractometer performing non destructive tests on elementary components, which are not suited (or allowed) for being analysed by traditional diffractometers or even on components that cannot be displaced from their original location.

PRIOR ART

Diffraction techniques are widely used in the field of analysis of material structure. The obtainable information by this technique are important in several fields, such as chemistry, metallurgy and metallography, extractive industry, transportation, environment, aeronautics, aerospace, buildings and even conservation of cultural heritage.

Several types of radiation are used for diffractometric analysis. Very common are the diffraction techniques by x-ray, electrons and neutrons. Particularly important are the techniques of x-ray diffraction.

Generally this kind of equipment is used to detect diffraction from powders or polycrystalline solids. Analysis on polycrystalline solids are especially interesting when investigation is required for components of industrial implants and/or implant in exercise.

This equipment requires an x-ray source, a specimen stage and x-ray detector. The specimen is requested to rotate, so that its surface is illuminated by the x-ray beam, coming from the source under different angles. The specimen and detector are requested to rotate simultaneously (optionally) at distinct rate so that their relative position allow the detector for receiving the diffraction beam to form the crystallographic planes which are in the right position for reflection.

X-ray diffractometry is useful to obtain information in the field of chemical composition, physical and mechanical characteristics of specimens (presence of residual stress or compression) of metal manufactured or other material. It is useful even for precocious detection of defects or damages of crystalline structure, for example, in welded components or under load or fatigue. Generally, this stress causes preferred orientation of crystalline lattice that can be detected by x-ray diffraction when particular procedures are adopted. This technique is useful even to analyse fibrous structures and glasses to determine the state of conservation and the chemical and physical characteristics.

It is sometimes useful to investigate by non destructive testing the lattice structure of components in implants on exercise. In this case, it is often difficult or impossible to obtain specimens for traditional analysis and laboratory tests. Often, it happens that the component or the implant under analysis can not be moved. For this reason, there is the necessity of a diffractometer, and in particular, an x-ray diffractometer that can be easily used without moving any structure or component of the implant. It is important that this diffractometer enables obtaining a considerable range of information (i.e. equivalent to the laboratory diffractometers to analyse powders and polycrystalline materials). In particular, it is useful to recognise the presence of stress, preferential orientations, structural defects of the material that constitute the component analysed, avoiding that the particular working condition of the diffractometer will constitute a limit for the attainable information. It means that it is necessary to develop a diffractometer that is useful for being used in place and improve the performance of the traditional laboratory diffractometers.

SUMMARY OF THE INVENTION

The above mentioned problems are overcome by a diffractometer comprising:
an analytical unit supporting a radiation source having a collimation axis; and a radiation detector having a reception axis, said collimation and reception axis converging in a centre, named centre of the diffractometer, which is fixed with respect to the analytical unit;
means for moving said analytical unit;
means for rotating said source and detector around said centre of the diffractometer Preferably, said means for moving said analytical unit permit to change the position in space of the centre of diffractometer.

According to a favourite embodiment of the invention, the diffractometer is an x-ray diffractometer.

Preferably, said means for rotating said source and detector are suitable to rotate source and detector, so that the axis of collimation and reception are contained in a equatorial plane. This plane is fixed with respect to the analytical unit.

According to a favourite embodiment of the invention, said analytical unit is supported by a supporting and movement structure and means are provided for moving said analytical unit with respect to the structure of support and movement, so that the analytical unit can rotate around an axis, called equatorial axis, contained in the equatorial plane and passing through the centre of the diffractometer. This fact corresponds to a rotation of the equatorial plane around the equatorial axis. This type of rotation is advantageously possible for an arc of at least 10°, preferably of at least 20° or even far higher values, for particular analytical necessity.

According to a preferred embodiment of the invention, the movement of this analytical unit with respect to the support and movement structure, permits the rotation of the equatorial plane with respect to the equatorial axis, without changing the axis position in the space.

The plane perpendicular to said equatorial axis and containing the centre of the diffractometer, is fixed with respect to the analytical unit, and it's called the axial plane. This plane can constitute a symmetry plane for said analytical unit.

A "source collimation axis" is commonly defined as the axis of the radiation beam that the source can emit, and a "reception axis", is commonly defined as the axis of the radiation beam that can be detected by the detector.

The invention also concerns a method of diffractometry, preferably of x-ray diffractometry comprising positioning a diffractometer as previously described with the centre of the diffractometer at a point of the surface of an element to be analysed.

According to a possible embodiment of the invention, the axial plane can be advantageously placed perpendicularly with respect to the surface of the analysed element at the point coincident with the centre of diffractometer.

According to an embodiment of the invention said analysed element is not mechanically connected to the diffractometer, with which, more preferably, it is not even in contact.

LIST OF THE FIGURES

DETAILED DESCRIPTION OF A POSSIBLE FORM OF IMPLEMENTATION

As an example an x-ray diffractometer according to the present invention is described.

Figure 1:
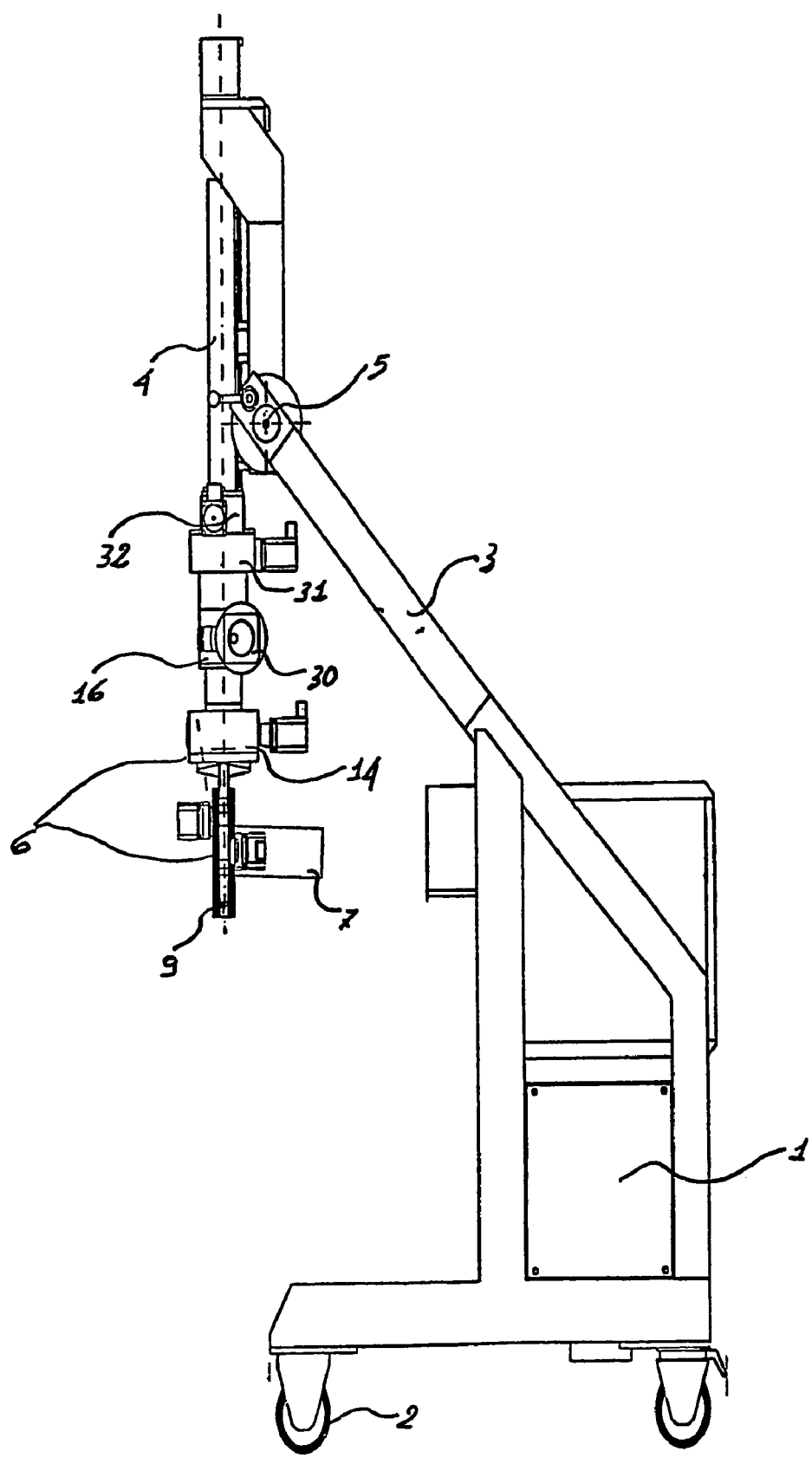
FIG. 1 represents schematically the lateral view of an x-ray diffractometer, according to the present invention.

The FIG. 1 shows a lateral view of a x-ray diffractometer, according to the present invention. The equipment includes a base (1), that can be equipped with two wheels (2) or other means for transportation and positioning and can also contain an electric generator capable of generating the energy required for the use, a tank of cooling liquid for the x-ray source and the electric components for positioning the movable parts and collecting data from the measurement equipment and also to process these data.

The equipment includes a support (3), an arm (4) supported by said support (3) and rotatable with respect to the arm, to permit a vertical positioning of the extremity (6) that includes the analytical unit, supported by the arm (4). Locking devices (5) permit fixing the arm (4) position with respect to the support (3). The extremity (6), also visible in FIG. 2 and FIG. 3, includes an x-ray source (7), an x-ray detector (8) and other positioning devices. These devices include the element (9), called primary Euler cradle, which may advantageously be in the form of a circular arch, devoted to support the x-ray source (7) and the detector (8). In the described case, the primary Euler cradle is the analytical unit. Source (7) and detector (8) can be conveniently moved along the primary Euler cradle (9). For each position reached on the primary Euler cradle by source and detector, the source collimation axis (11) and the reception axis (10) are always directed towards a point (12), which is the centre of the diffractometer (12) and can advantageously coincide with the centre curvature of the primary Euler cradle (9).

Figure 3:
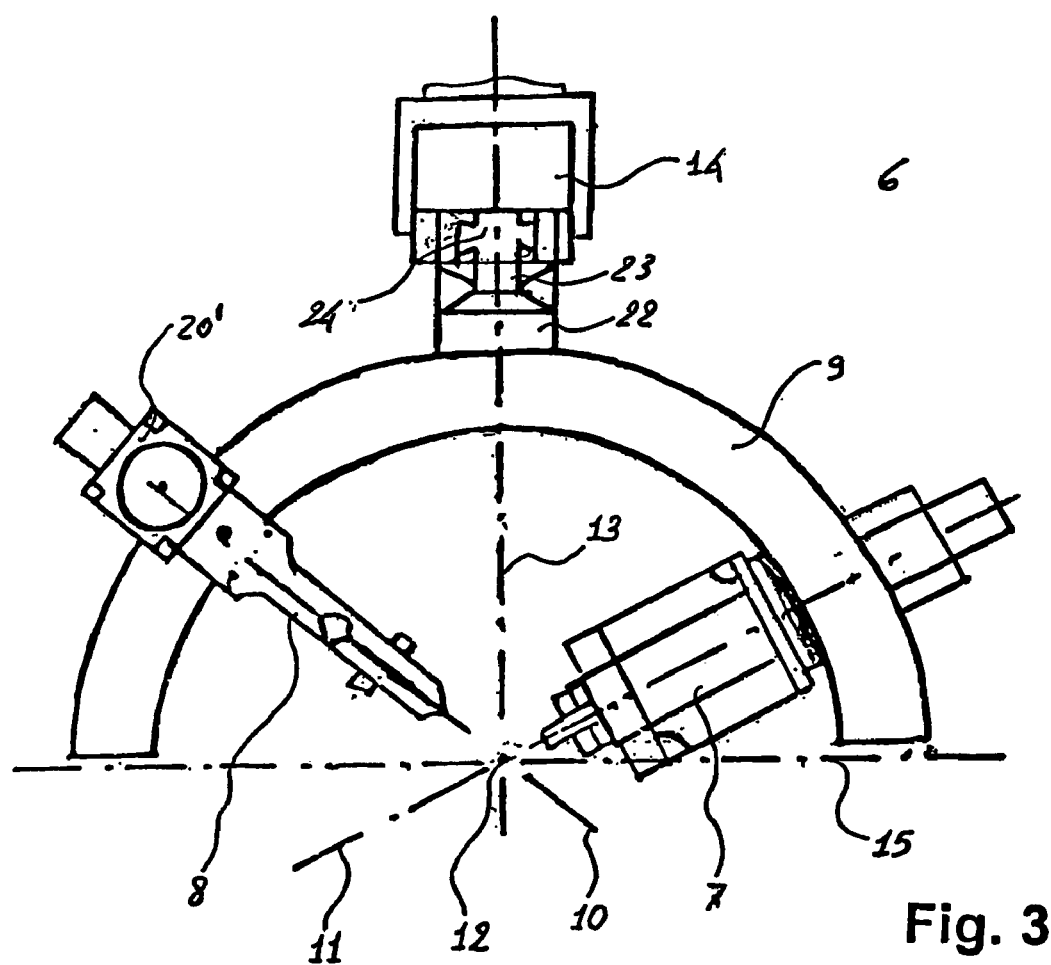
FIG. 3 represents schematically a detail of the diffractometer of FIG. 1, more specifically, the extremity of the diffractometer that includes the first analytical unit supporting the source and the x-ray detector.

The axes (10) and (11), can thus rotate the centre (12) in a plane, the equatorial plane, that is substantially parallel to the primary Euler cradle (9). In FIG. 3 the equatorial plane coincides with the plane of the drawing, the axial plane is perpendicular to the equatorial plane, their intersection is the axis (13), called exploration axis.

According to a preferred embodiment of the invention, said primary Euler cradle (9)

According to a preferred embodiment of the invention, said primary Euler cradle (9) is conveniently supported by a supporting and movement structure (14), called secondary Euler cradle. A special system permits the primary Euler cradle (9) to be moved with respect to the secondary Euler cradle (14) to execute a rotation around the equatorial axis (15). This equatorial axis (15) is contained in the equatorial plane and is perpendicular to the exploration axis (13). In this way, the whole equatorial plane can rotate of a certain angle with respect to the equatorial axis (15), and thus the collimation axis (10) and the reception axis (11) can rotate because the source (7) and the detector (8) are supported by the primary Euler cradle (9).

Figure 4:
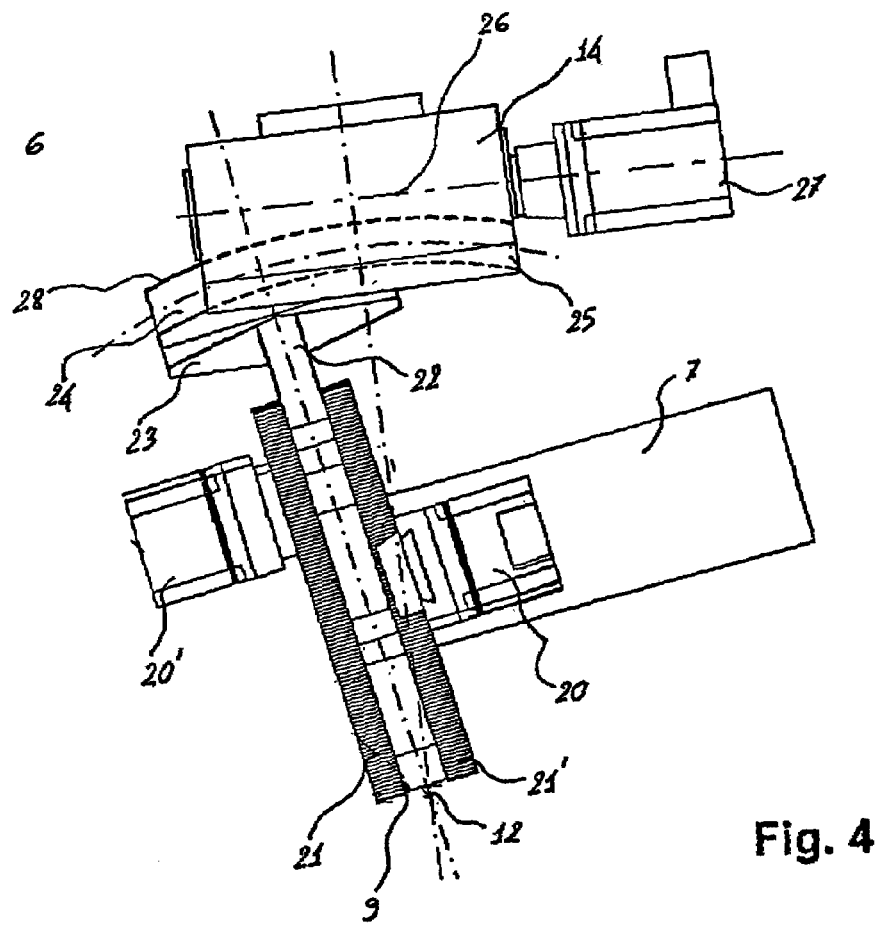
FIG. 4 represents schematically the lateral view of the detail of the diffractometer of FIG. 1 comprising the first analytical unit supporting the source and the x-ray detector and the structure for supporting and moving the analytical unit.

FIG. 4 shows a lateral view of the extremity (6) that includes the two Euler cradles, and shows a possible implementation of the articulation mechanism of the primary Euler cradle (9) with respect to the secondary Euler cradle (14). The primary Euler cradle (9) includes two cog arcs (21) and (21'), suitably joined. The source (7) and the detector (8) move along these arcs through a gear moved by electrical motors 20 and 20', which are part of source and detector. a support (22), jointed to the primary Euler cradle (9), supports it to the secondary Euler cradle (14). The support (22) has a portion (23) having a dovetail shaped structure (24), said structure running in a correspondent cavity (25) (dashed in FIG. 4) of the secondary Euler cradle (14), thus permitting the movement of rotation of the equatorial plane, as above discussed. An endless screw (not shown) is set parallel to the axis (26) and moved by a motor (27) and mates with a correspondent thread obtained on the upper surface (28) of the dovetail structure (24). This endless screw promotes the rotation of the primary Euler cradle (9). This, like other types of mechanism can be easily implemented by a technician of the field.

A series of movement devices for positioning in the space the extremity (6) that include the two Euler cradle is also foreseen.

Figure 2:
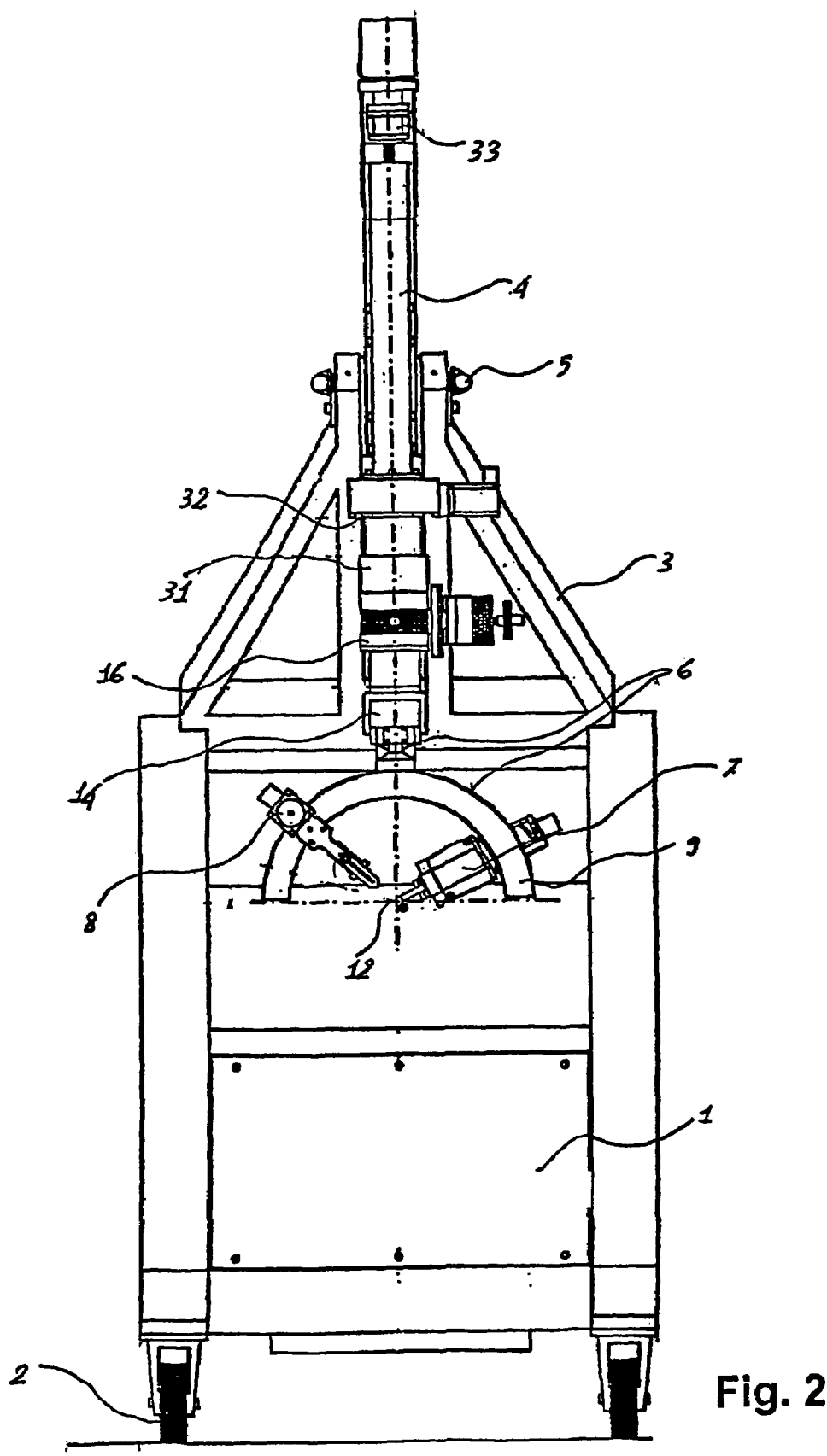
FIG. 2 represents schematically the frontal view of the diffractometer of FIG. 1.

With reference to FIG. 2, the system (16) equipped with a motor 30, permits the complete rotation, around the arm axis (4) of this extremity (6). This permits a very advantageous instrument positioning, and also provides the possibility of exploring the material to be analysed along different directions.

With reference marks (31) and (32), two slides are identified; they permit mutually perpendicular translation movements; this movement is also perpendicular to the arm axis (4); these slides are also moved by special motors.

The motor (33), through a screw mechanism, permits the translation of the arm 4 along its axis.

Figure 5:
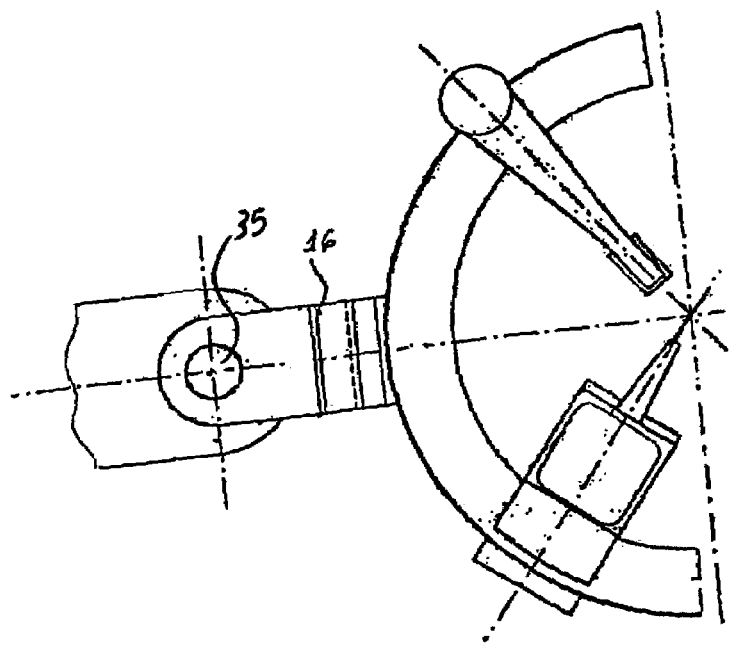
FIG. 5 represents schematically an articulation able for moving said analytical unit in the space, according to a particular embodiment of the invention.

Other moving devices could be provided to facilitate the positioning of the extremity (6). For example an articulation can be provided, preferably between the device (16) and the system of slides (31) and (32), permitting a rotation around an axis perpendicular to the arm axis (4). In FIG. 5, this articulation is schematically represented by mark (35) and is set above the pivot (16) (schematically indicated). This articulation permits a rotation of 180° and can be conveniently moved by a special motor.

Instead of the support (3) a vertical support can be provided, along which arm (4) may translate vertically thanks to a special device. This vertical support could rotate around its axis, thus giving a further freedom degree to the structure positioning. It's apparent that equipment can be implemented with different kinds of moving devices, according to the investigation requirements.

On the primary Euler cradle (9) pointing devices can be provided for positioning the instrument correctly with respect to the element under investigation. As described above, this element under analysis may be a component of an operating structure, for example part of an industrial plant, or also an element too big dimensions to be moved, and that requires a not destructive structural control. The pointing device can include two lasers fixed on the primary Euler cradle and pointed towards the centre of the diffractometer (12), and a telecamera, also fixed on the primary Euler cradle and pointed along the axis of exploration (13). The overlap of the two spots projected by the laser on the surface of the element analysed, and their shape will is indicate the correct positioning of the equipment with respect to the element analysed. Advantageously, the moving part may be moved by special motors, controlled by electronic systems. These systems can collect data from the pointing device and manage completely the positioning of the equipment.

Also the movement of the source and of the x-ray detector may be managed by an electronic system, as well as the movement of the primary Euler cradle can be electronically controlled respect to the secondary.

Source and detector can be of different types, chosen among those commonly used in the diffraction field. These types include all the suitable collimation system (slits, beams conditioning, and also monochromators if necessary). In particular, the detector can include a slide system that permits the movement of the collimation system (i.e. "capillary optic", "poly-capillary", etc.) along the reception axis of the beam, from and towards the centre of the diffractometer.

The choice depends on the type of radiation used and on the characteristic of the element analysed, as well as constructive problems of the equipment. In particular, in the case of x-ray diffraction, the detector can be either a scintillation detector, a solid state or any other known device. According to a possible embodiment, a ionisation detector of gas, such as a Geiger counter, can be used because of their reduced dimensions. According to a preferred embodiment of the invention it's possible to use a Geiger counter in its field of proportionality, also called proportional counter. Furthermore, source and detector can be equipped with devices that permit their shifting the collimation and reception axes respectively, to regulate, outside said source and detector, the optic path of the beam incident on the material to be analysed and diffracted beam, according to operating requirements.

The dimension of the equipment can be chosen in relation to the application the instrument is built for and be such that all the devices are suitably supported. In particular, as far as the primary Euler cradle is concerned, they must be sufficient to adequately support source and detector in relation to their dimensions and to permit a sufficient excursion along the primary Euler cradle itself. It's also important to keep in mind that, by increasing the size, the required power of the motors increases, to move the structures without the risk of vibration.

For example, it has been possible to implement an equipment as described with an external radius of the primary Euler cradle of about 22 cm, an excursion of source and detector, of the proportional ionisation kind, of about 135°, with a distance of about 11 cm between the centre of the diffractometer and the source and between the centre of the diffractometer and detector. Through analysis of reference specimen, results were obtained in harmony with those of traditional diffractometers.

The structure can also include electric connection and connections for transmitting data between the electronic control systems and the various devices of movement or detection above described, and also pipes for the cooling liquid for the source of x-ray.

According to a possible method of using the diffractometer, the latter is placed so that a point of the surface of the element to be analysed is at the centre of the diffractometer (12). When starting, that surface shall be perpendicular to the exploration axis (13); when the surface is not flat, the plane tangent to the surface, called specimen plane, shall be perpendicular to the exploration axis. Thus the collimation axis (11) forms an angle θ with the specimen plane. The reception axis (10) will form an angle θ with the specimen plane and 2θ with respect to the collimation axis. The system is thus able to detect the rays reflected by families of crystallografic planes, that have a interplanar distance d that, for an angle θ correspondent to the relative position of the source and detector, satisfies the Bragg's law $n\lambda=2d^*\sin\theta$, where n is a whole number and λ the wavelength of the x-ray beam emitted from the source.

According to a possible operating method, the collimation axis (11) and the reception axis (10), perform the above mentioned rotation by keeping themselves symmetric with respect to the exploration axis (13); thus, it is possible to detect the diffraction beam from various families of lattice planes satisfying the Bragg law at different angles θ.

When the specimen is a polycrystalline solid with enough small crystals, as it is common, the various families of planes may be randomly oriented in all the directions. So by scanning various angles θ, the various families of planes that satisfy Bragg law can be detected. By a rotation of the equatorial plane, around the equatorial axis (15), as above mentioned, and by keeping unvaried the position of the source and detector with respect the axis of exploration (13) (that will be rotated of ω together with the equatorial plane), The equatorial plane will be no longer perpendicular to the specimen plane. It is thus possible to scan again the different angles θ, and detect signals from the planes inclined of an angle ω with respect to the specimen plane. The comparison at different θ angles of diffraction intensities at the same θ angle (corresponding to plane families with the same interplanar distance), give an information on the possible preferred orientations in the crystalline structure. This is equivalent to explore for a certain arc the Debye circle.

Alternatively, the collimation and reception axes can be kept symmetrical with respect to an axis laying on the equatorial plane and different from the exploration axis to analyse families of planes with different inclinations with respect to the exploration axis. This is important when monocrystalline materials have to be analysed, or if it's impossible to position the exploration axis perpendicular to the specimen plane, or when special directions in the materials have to be analysed.

The number of different possible positioning of the equipment confers a great versatility to the use of the diffractometer.

When the specimen can be at least partly moved or orientable in the space the analysis opportunities are extended, so that a range of information that are comparable to those obtained from traditional laboratory instruments may be such obtained, such as single crystal instruments which have the highest number of freedom degrees for orienting the specimen in the space.

It has been described in particular a diffractometer, and a method for its use, in which the radiation used are x-ray. This constitutes a preferred embodiment of the invention. Anyway, with equipment built with special dimension and features, it's possible to use different kinds of sources and detectors of other kinds of radiation, such as electromagnetic, acoustics or consisting of particle beams.

The invention claimed is:

1. A diffractometer comprising:
    a base;
    an analytical unit supporting a source of a radiation beam having a collimation axis and a radiation beam detector having a reception axis;
    said collimation and reception axes converging at a centre of the diffractometer;

said centre of the diffractometer being fixed with respect to said analytical unit;

means for moving said analytical unit with respect to said base;

means for rotating said source and said radiation beam detector around said centre of the diffractometer so that said collimation axis and said reception axis are kept in an equatorial plane, fixed with respect to said analytical unit;

a support and movement structure supporting said analytical unit;

means for moving said analytical unit with respect to said support and movement structure so that said analytical unit can rotate around an equatorial axis contained in said equatorial plane and passing through said centre of the diffractometer;

said means for moving said analytical unit with respect to said support and movement structure permitting the rotation of the equatorial plane around said equatorial axis, without said support and movement structure changing its position ; and wherein said means for moving said analytical unit with respect to said base moves said analytical unit to change a position of said equatorial axis with respect to said base.

2. The diffractometer according to claim 1, wherein said means for moving said analytical unit with respect to said base enables rotation of said analytical unit around an axis perpendicular to said equatorial axis.

3. The diffractometer according to claim 1, wherein said source is a source of electromagnetic radiation, acoustic radiation, or radiation consisting of particle beams and said detector is a detector of electromagnetic radiation, acoustic radiation, or radiation consisting of particle beams.

4. The diffractometer according to claim 3, wherein said detector is a proportional ionization counter.

5. The diffractometer according to claim 1, wherein said source is an x-ray source and said detector is an x-ray detector.

6. The diffractometer according to claim 1, wherein said means for moving said analytical unit with respect to said base permits changing a position of said centre of the diffractometer by rotation or translation of said analytical unit.

7. The diffractometer according to claim 1, wherein said equatorial axis is perpendicular to a symmetry plane of said analytical unit.

8. The diffractometer according to claim 1, wherein the rotation around said equatorial axis is along an arc of at least 10°.

9. The diffractometer according to claim 1, comprising a pointing device placed on said analytical unit for positioning said analytical unit with respect to an element to be analysed.

10. The diffractometer according to claim 9, wherein said pointing device comprises two lasers and a telecamera.

11. The diffractometer according to claim 1, wherein said analytical unit is formed as a circular arc.

12. A diffractometry method comprising:

positioning a diffractometer including a base, an analytical unit supporting a source of a radiation beam having a collimation axis and a radiation beam detector having a reception axis, the collimation and reception axes converging at a centre of the diffractometer, the centre of the diffractometer being fixed with respect to the analytical unite, means for moving the analytical unit with respect to said base, means for rotating the source and the radiation beam detector around the centre of the diffractometer so that the collimation axis and the reception axis are kept in an equatorial plane, fixed with respect to the analytical unit, a support and movement structure supporting the analytical unit, means for moving the analytical unit with respect to the support and movement structure so that the analytical unit can rotate around an equatorial axis contained in the equatorial plane and passing through the centre of the diffractometer, the means for moving the analytical unit with respect to the support and movement structure permitting the rotation of the equatorial plane around the equatorial axis without the equatorial axis changing its position and the means for moving the analytical unit with respect to said base moving said analytical unit to change a position of said equatorial axis with respect to said base; and positioning the centre of the diffractometer on a point of a surface of an element to be analyzed.

13. The method according to claim 12, wherein the analytical unit has a symmetry plane and the symmetry plane is placed perpendicularly to the surface of the element to be analyzed at the point coincident with the centre of the diffractometer.

14. The method according to claim 12, wherein the radiation beam is an x-ray beam.

15. The method according to claim 12, wherein the element to be analyzed is not mechanically linked to the diffractometer.

* * * * *